United States Patent [19]

Kraus

[11] 3,954,174

[45] May 4, 1976

[54] UNITARY TWO-COMPARTMENT PACKAGE FOR STERILE SURGICAL ARTICLES

[75] Inventor: Robert G. Kraus, Parsippany, N.J.

[73] Assignee: Becton, Dickinson and Company, East Rutherford, N.J.

[22] Filed: Sept. 23, 1974

[21] Appl. No.: 508,143

[52] U.S. Cl. ............................. 206/223; 206/439
[51] Int. Cl.² ..................... B65D 79/00; A61L 1/00
[58] Field of Search ................. 206/223, 210, 439

[56] References Cited
UNITED STATES PATENTS

| | | | |
|---|---|---|---|
| 2,627,341 | 2/1953 | Morgan ............................ | 206/439 |
| 3,061,087 | 10/1962 | Scrivers et al. .................. | 206/439 |
| 3,332,549 | 7/1967 | Powell ............................ | 206/363 X |
| 3,472,369 | 10/1969 | Schuster ......................... | 206/439 |
| 3,613,879 | 10/1971 | Kemble ........................... | 206/210 |
| 3,730,338 | 5/1973 | Chesky .......................... | 206/223 X |

*Primary Examiner*—Leonard Summer
*Attorney, Agent, or Firm*—Kane, Dalsimer, Kane, Sullivan and Kurucz

[57] ABSTRACT

Disclosure is made of a unitary two-compartment package for sterile surgical articles which comprises; two separate and sealed containers, each defined by walls of sheet material which are permeable to a means of bacterial sterilization for surgical articles contained within the containers; and means such as an adhesive strip associated with at least one of the containers for permanently joining the two containers to each other.

3 Claims, 5 Drawing Figures

3,954,174

UNITARY TWO-COMPARTMENT PACKAGE FOR STERILE SURGICAL ARTICLES

BACKGROUND OF THE INVENTION

1. Field of the Invention

The invention concerns a method of packaging and packages produced thereby; and more specifically concerns the packaging of surgical articles which must be contained under sterile and/or aseptic conditions.

2. Brief Description of the Prior Art

The packaging of surgical articles and like materials which are subsequently sterilized and maintained under aseptic conditions within the package is well-known; see for example U.S. Pat. Nos. 3,332,549; 3,338,400; 3,490,580; 3,613,879; and 3,697,223. In general, the prior art methods and packages are designed to contain articles which may be sterilized by the same means. When it is desired to provide in a single unit, diverse sterile articles which require different methods of sterilization, the most common practice heretofore has been to package the diverse articles separately. The separate packages are then sterilized and packaged together in a third package which may be sterilized again if subsequent use demands that the inner packages themselves be maintained under sterile conditions.

By the package and method of my invention it is now possible to package surgical articles in a single unit, even if the articles are diverse in nature and require diverse means of sterilization. This is accomplished without the need for containing the packaged diverse articles in a third package and also assures that the desired articles will remain together in a single unit.

SUMMARY OF THE INVENTION

The invention comprises a unitary two-compartment package for sterile surgical articles which comprises; two separate and sealed containers, each defined by walls of sheet material which are permeable to a means of bacterial sterilization for surgical articles contained within said containers; and means associated with at least one of said containers for permanently joining said containers to each other.

The invention also comprises a method of packaging diverse surgical articles which require diverse means of sterilization, in a single unitary package which comprises; sealing those articles which can be sterilized by a first method in a first container of sheet material and sterilizing the articles in said first container; sealing those articles which may be sterilized by a second method in a second container of sheet material and sterilizing the articles in said second container; and permanently joining said first and second containers to form a single unitary package.

The term "permanently joining" as used herein means joining the components in such a manner that separation will destroy the package structure.

DETAILED DESCRIPTION OF THE INVENTION

A complete understanding of the invention is conveniently obtained by referring now to those embodiments of the invention illustrated in the accompanying drawings.

Figure 1:
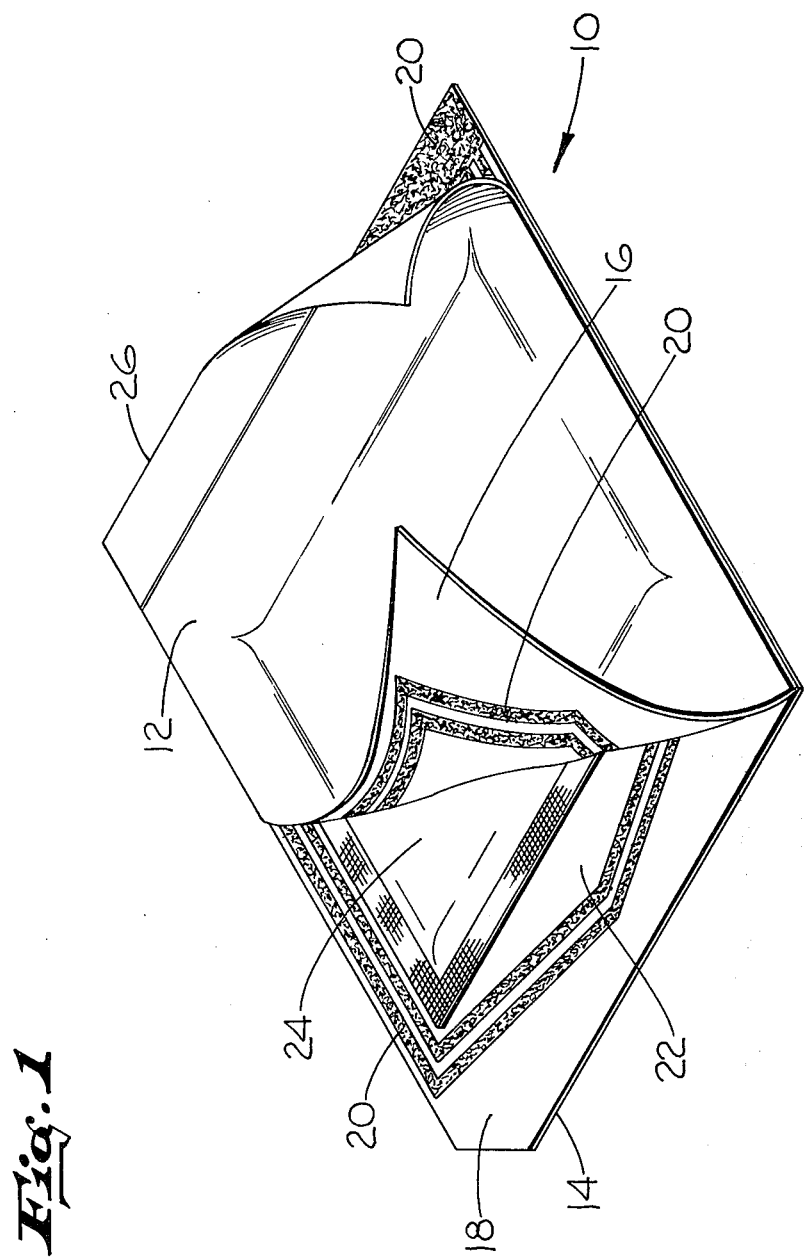
FIG. 1 is an overall view of one component of a package within the scope of the invention.

With reference first to FIG. 1, an isometric view of a component part of the embodiment package of the invention, there is seen member 10 of a unitary package shown to comprise an upper layer 12 and a lower layer 14 of flexible sheet material. Examples of flexible sheet material which may be employed are flexible sheets of metal foil such as aluminum foil, paper, synthetic polymer films such as films of polyethylene, polypropylene, polyacrylates and like sheet materials conventionally employed in the packaging art. The inner surfaces 16 and 18 of layers 12 and 14 respectively, bear an adhesive sealing medium disposed about the periphery of the sheet layers 12 and 14. In FIG. 1 upper layer 12 has been partially peeled back on the corners to show the inner surfaces 16 and 18 bearing sealing medium 20. It is not necessary that both upper layer 12 and lower layer 14 bear the sealing medium 20, but at least one of layers 12 and 14 will bear the sealing medium 20 so that when layers 12 and 14 are brought together they may be sealed in a sealing zone disposed about the periphery of the two sheet layers. The sealing medium 20 may be any adhesive sealant which will form a permanent hermetic seal but which will unseal by peeling sheet layers 12 and 14 apart. Such adhesive sealants are well-known in the art and include for example pressure sensitive resin adhesives, thermosetting adhesives, and curable resin adhesive mixtures. Such adhesive sealants and the method of employment are generally well-known and need not be described here. A central compartment 22 is defined by layers 12 and 14 and the sealing zone established by sealing medium 20. This compartment 22 contains a surgical article or articles 24 such as for example surgical instruments, sponges, germicidal solutions in appropriate containers, sutures, applicators and the like. The upper layer 12 is shown to have an extension 26. The member 10 constitutes one of the containers comprising the multi-container package of the invention.

Figure 2:
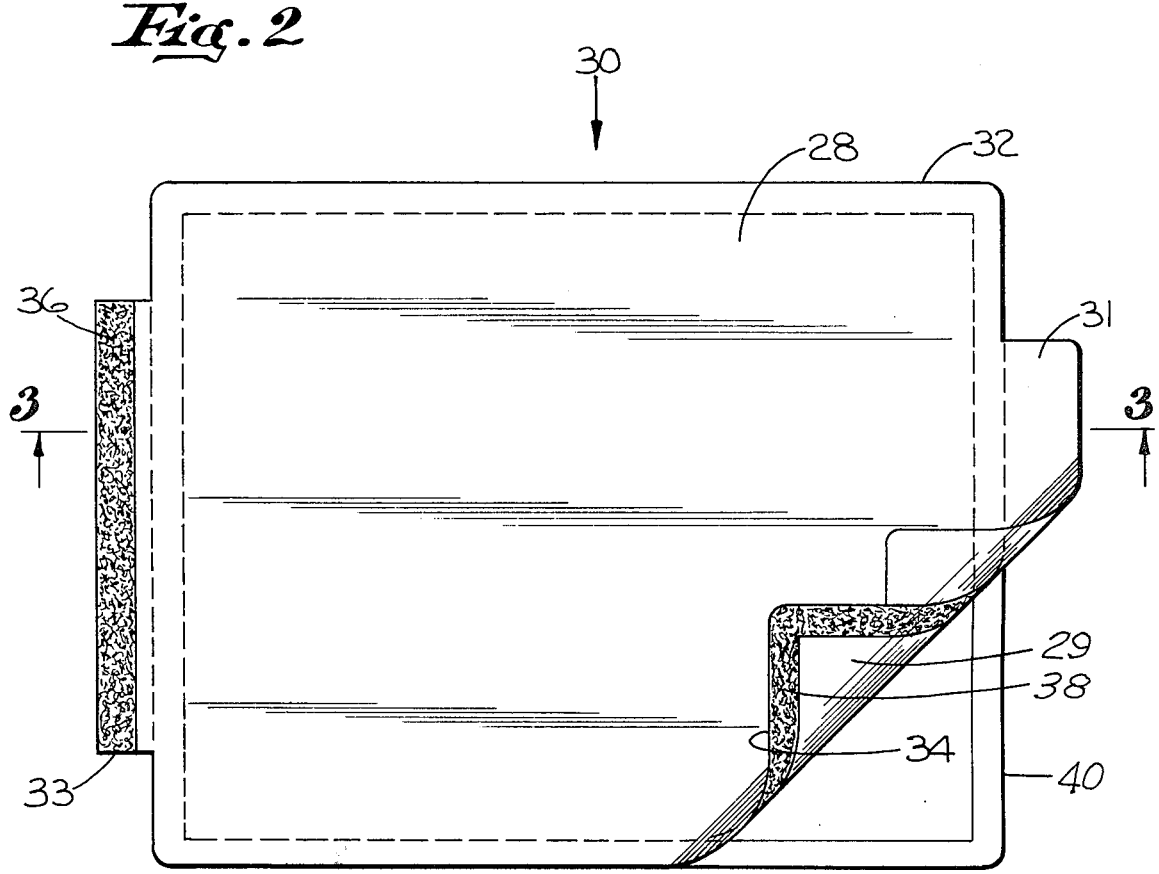
FIG. 2 is an overall view of a second component of a package within the scope of the invention, shown open.

FIG. 2 is a partial isometric view of a second component 30 which together with member 10 forms an embodiment package of the invention as seen from above. The member 30 comprises a flexible sheet 32 having upper surface 28 and lower surface 29 and may be fabricated from the same material as member 10 or may be a different sheet material. As shown in FIG. 2, the lateral edge 34 of surface 29 bears a sealing material 38. Tabs 31 and 33 are advantageously placed on opposing sides of sheet 32 and the upper surface 36 of tab 33 also bears sealing material 38. The adhesive sealing material 38 employed may be the same sealing material 20 employed in the fabrication of member 10. Sheet 32 is a closure for a tray member 40 (not seen in FIG. 2) and with tray 40 forms and defines an interior compartment 44 for receiving surgical instruments and like materials to be maintained under sterile conditions. Tray 40 may be fabricated from any flexible sheet material, such as that employed in fabricating sheet 32 but preferably is of heavier constitution and by comparison relatively inflexible.

Figure 3:
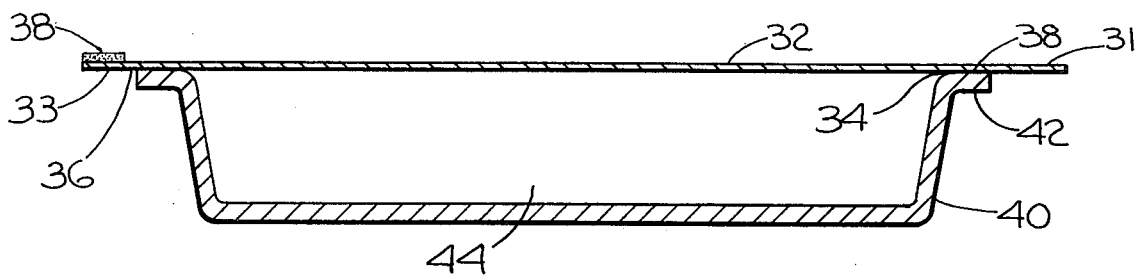
FIG. 3 is a cross-sectional view along lines 3—3 of FIG. 2.

FIG. 3 is a cross-sectional view along lines 3—3 of FIG. 2 and more clearly shows the relationship of sheet 32 as a closure for tray 40. As seen, tray 40 has a flange 42 disposed about the upper periphery of integral sidewalls 50 and which mates with the sealant 38 bearing surface 34 of sheet 32 to effect a sealed compartment 44. Sheet 32 is employed as a closure after the desired materials for sterilization are placed in the compartment 44. The tab 31 is an extension of sheet 32 and provides a convenient means for opening the component 30 when access to the contained articles is desired.

Figure 4:
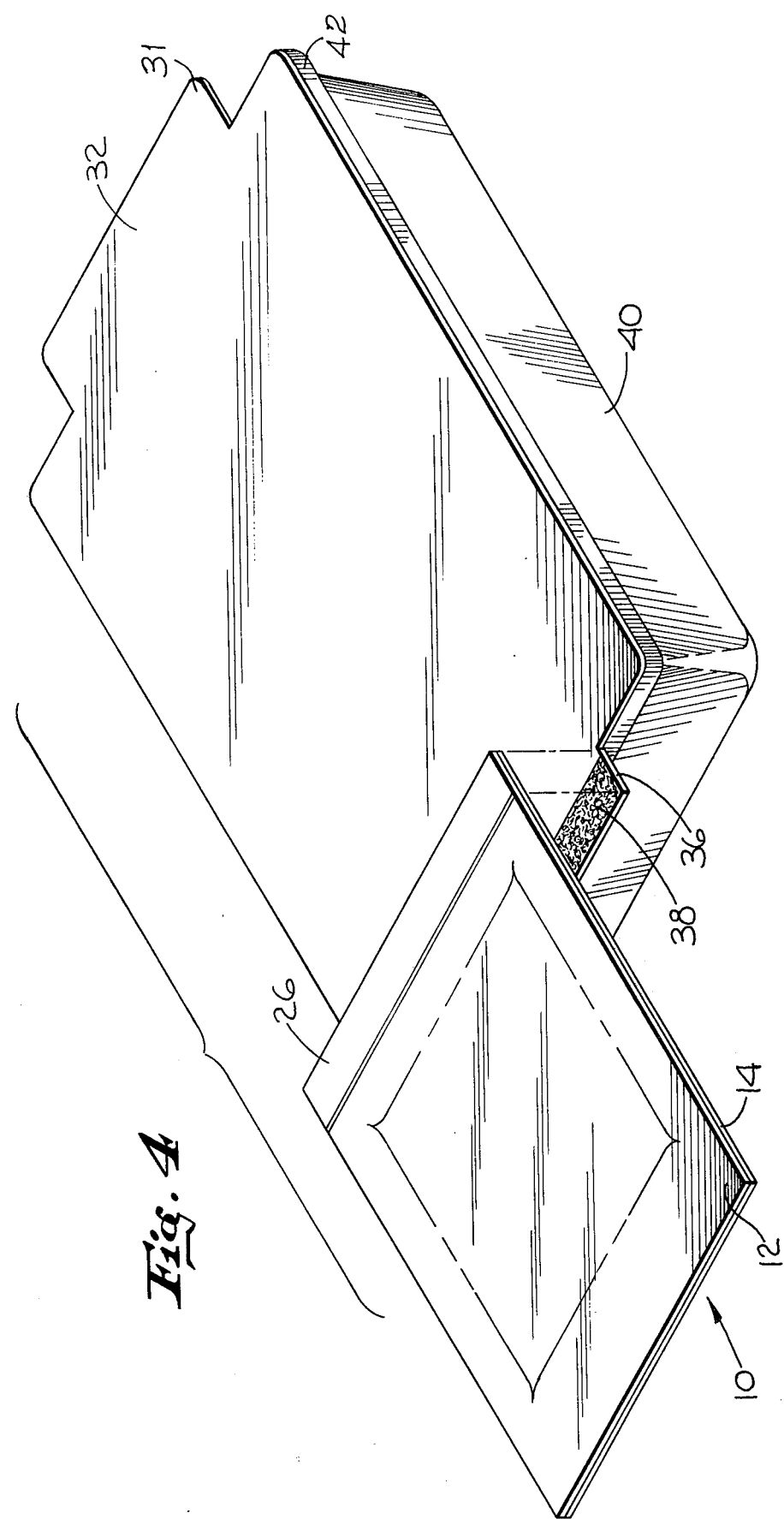
FIG. 4 is an overall view of the components of the package of the invention as seen in FIGS. 1 and 2, positioned for permanent joinder.

FIG. 4 is an isometric view of the component containers of the package of the invention positioned prior to their permanent joinder and clearly shows container member 10 of FIG. 1 positioned for attachment to the sealant bearing surface 38 of tab 36 on sheet 32 by the extension 26 of one of the layers 12 and 14 of member 10.

Figure 5:
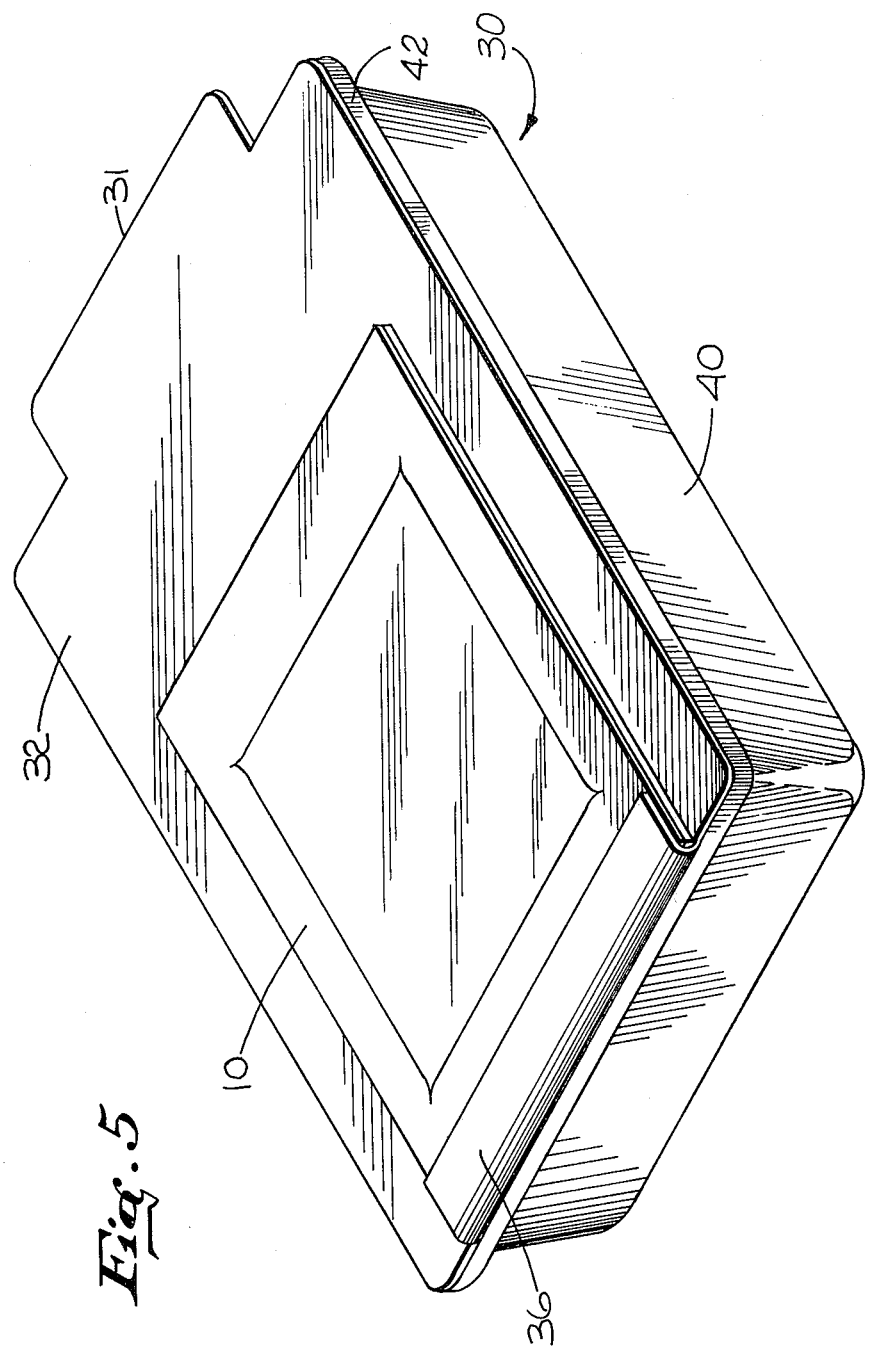
FIG. 5 is an overall view of a package of the invention as seen in FIG. 4, but with both compartments joined to provide the single unitary package.

FIG. 5 is an isometric view of the unitary embodiment of the invention showing the component containers joined together, and member 10 folded upon member 30 for convenience in handling.

The method of the invention is carried out by first sealing those surgical articles which can be sterilized by a first means into member 10 prior to its attachment to member 30. The contained article is then sterilized, the walls being permeable to the means of sterilization. As an example, germicidal liquids enclosed in impervious foil sachets may be sealed into compartment 22 of member 10 and sterilized by exposure to cobalt radiation. This means of sterilization is generally employed as the most efficient for sterilization of germicidal liquids. In a separate step, other articles which are desirably included with the germicidal solution such as for example surgical drapes and/or applicators are sealed in compartment 44 of the member 30 and sterilized with, for example, a sterilization gas such as ethylene oxide. In general, gas sterilization has been found to be an efficient and effective means of sterilizing such articles and in this instance at least the closure member 32 of the member 30 will be pervious to ethylene oxide sterilizing gas. The members 10 and 30 may then be permanently joined to provide a unitary surgical package, by adherence along an adhesive bearing zone of one or both members. In use, the member 30 may be opened first by peeling the adhered sheet 32 open using tab 31 to gain access to the articles contained. Member 10 is then opened by peeling cover layers 12 and 14 apart to gain access to the contained article in compartment 22. The surgeon then has assurance that the surgical articles required for a given procedure are all together in a single unitary package even though such articles may be diverse in nature and desirably or necessarily sterilized by diverse means. The fact that separation of the adhesive bond joining the component compartments destroys the package is an added safety factor, warning the user that the complement of packaged articles may be incomplete.

What is claimed is:

1. A unitary two-compartment package for enclosing sterile surgical articles, wherein the articles in each compartment require sterilization by diverse means, which comprises:

two separate and sealed containers, each defined by walls of sheet material and each of which is permeable to a different means of bacteria sterilization for surgical articles contained within said containers; said containers being permanently joined to each other.

2. The package of claim 1 wherein the walls of said containers are partly of flexible sheets and partly of relatively inflexible sheets.

3. A unitary two-compartment package for sterile surgical articles wherein the articles in each compartment require sterilization by diverse means, which comprises:

a. a first member which comprises,
 1. two layers of sheet material, at least one of which bears a sealing medium around the periphery of its inner surfaces to form a sealing zone between said layers, said sealing medium being capable of unsealing by peeling said layers of sheet material from each other, at least one of said layers being permeable to a first means of sterilization;
 2. a central compartment defined by the layers of sheet material and said sealing zone; and
 3. an extension of at least one of said layers of sheet material beyond the outer periphery of said sealing zone; and b. a second member which comprises,
 1. a flexible sheet;
 2. a tray of sheet material having integral sidewalls on the periphery thereof and a flange radially disposed around the periphery of the upper portion of said sidewalls, at least one of said flexible sheet and said tray of sheet material being permeable to a second means of sterilization, said flexible sheet being adapted to mate with said flange and to form a closure for the open recess formed by said tray;
 3. a sealant material disposed on at least one of said flexible sheet and said flange in a zone where said flange and said flexible sheet mate so as to adhere said flange to said flexible sheet;
 4. a flat extension of said flexible sheet beyond the periphery of said flange; said first and second members being permanently joined along their respective extensions (a) 3 and (b) 4.

* * * * *